US00PP31405P2

(12) United States Plant Patent
Slaughter et al.

(10) Patent No.: US PP31,405 P2
(45) Date of Patent: Jan. 28, 2020

(54) NECTARINE TREE NAMED 'BURNECTTHIRTYFOUR'

(50) Latin Name: ***Prunus persica* var. *nucipersica***
Varietal Denomination: Burnectthirtyfour

(71) Applicant: WAWONA PACKING CO., LLC, Cutler, CA (US)

(72) Inventors: John K. Slaughter, Fresno, CA (US); Timothy J. Gerdts, Kingsburg, CA (US)

(73) Assignee: Wawona Packing Co, LLC, Cutler, CA (US)

( * ) Notice: Subject to any disclaimer, the term of this patent is extended or adjusted under 35 U.S.C. 154(b) by 0 days.

(21) Appl. No.: 15/998,164

(22) Filed: Jul. 11, 2018

(51) Int. Cl.
*A01H 5/08* (2018.01)
*A01H 6/74* (2018.01)

(52) U.S. Cl.
USPC ..... Plt./190

(58) Field of Classification Search
USPC ..... Plt./190
CPC ..... A01H 5/08; A01H 5/0856; A01H 5/0868; A01H 5/00; A01H 6/74; A01H 6/7454
See application file for complete search history.

(56) References Cited

U.S. PATENT DOCUMENTS

PP13,589 P2 * 2/2003 Gerdts ..... A01H 6/7454 Plt./190

* cited by examiner

*Primary Examiner* — June Hwu
(74) *Attorney, Agent, or Firm* — Potter Anderson and Corroon LLP

(57) ABSTRACT

A new and distinct variety of nectarine tree (*Prunus persica* var. *nucipersica*), which is denominated varietally as 'Burnectthirtyfour', and which produces an attractively colored yellow-fleshed, clingstone nectarines which is mature for harvesting and shipment approximately September 10 to September 21 under the ecological conditions prevailing in the San Joaquin Valley of central California.

1 Drawing Sheet

Botanical designation: The present invention relates to a new, novel, and distinct variety of nectarine tree, '*Prunus persica* var. *nucipersica*'.

Varietal denomination: 'Burnectthirtyfour'.

BACKGROUND OF THE NSW VARIETY

The present variety of nectarine tree resulted from an on-going program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled and hybrid cross pollinations each year to produce seedling populations from which improved progenies are evaluated and selected.

The seedling, 'Burnectthirtyfour' was originated by us, and selected from a population of seedlings growing in our experimental orchards which are located near Fowler, Calif. The seedlings, grown on their own roots, were derived from planting seed of a Burchell seedling, U.S. Plant Pat. No. 13,589, titled "Nectarine tree named 'Burnectseven'" used as the female parent. The pollen parent of this seedling was from a non-patented seedling, 'E49.006'. The resulting fruit was collected from the female parent at a mature stage and seeds were extracted in August of 2003. After a period of stratification, the seed was placed in the greenhouse by population, and then field planted for tree establishment, and ultimately to exhibit fruit for evaluation. One yellow-fleshed nectarine seedling, which is the present variety, exhibited especially desirable characteristics, and was then designated as 'M17.023'. This seedling was marked for subsequent observation. After the 2005 fruiting season, the new variety of nectarine tree was selected for advanced evaluation and repropagation.

ASEXUAL REPRODUCTION

Asexual reproduction of this new and distinct variety of nectarine tree was accomplished by budding the new nectarine tree onto 30 trees of 'Nemaguard' Rootstock (unpatented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Burnectthirtyfour' is a new and distinct variety of nectarine tree, which is considered of relatively large size, and which has a vigorous growth characteristic. This new tree is also a regular and productive bearer of relatively large, firm, yellow-fleshed, acidic clingstone fruit which have a very good flavor, and eating qualities. This new nectarine tree has a medium chilling requirement of approximately 600 hours, and further produces relatively uniformly sized fruit throughout the tree's canopy. In addition to the foregoing, the fruit of the new nectarine also appears to have good handling and shipping qualities. The 'Burnectthirtyfour'

Nectarine tree bears fruit which are typically ripe for commercial harvesting and shipment on approximately September 10 to September 21 under the ecological conditions prevailing in the San Joaquin Valley of central California. In relative comparison to the 'September Free' nectarine tree (USDA Unpatented), which is the closest known variety, the current variety produces fruit that is clingstone. Further the current variety exhibits a more oblate shape than the 'September Free' nectarine tree, used as the commercial comparative variety. In relative comparison to the 'Burnectseven' (U.S. Plant Pat. No. 13,589) seed parent tree, the current variety is contrasted by considered as having a more external blush and a more lustrous finish whereas the seed parent exhibits skin finish that is duller. Further the current variety ripens 7-8 weeks later than the seed parent. In relative comparison, the current variety expressed a fruit diameter that is generally 5.0 millimeters larger than the un-patented 'E49.006' nectarine pollen parent. Further the current variety exhibits a clingstone character and the 'E49.008' pollen parent is freestone.

BRIEF DESCRIPTION OF THE DRAWINGS

The accompanying drawing, which is provided, is a color photograph of two whole mature fruit in their fifth year displaying both the apical and basal aspects thereof. One mature is fruit bisected transversely through the equatorial plane, and which reveals the flesh color, and stone characteristics thereof. The external coloration of the fruit as shown in the photograph is sufficiently matured for harvesting and shipment. Additionally, the photograph displays a sample vegetative shoot bearing typical leaves, and a typical stone with the flesh removed. The colors in these photographs are as nearly true as is reasonably possible in a color representation of this type. Due to chemical development, processing and printing, the leaves and fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. § 112, and does not constitute a commercial warranty, (either express or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of nectarine tree, the following has been observed during the tenth fruiting season, and under the ecological conditions prevailing at the orchards of the assignee which are located near the town of Fowler, county of Fresno, state of California. All major color code designations are by reference to The R.H.S. Colour Chart (Royal Horticultural Society, Fourth Edition, 2001) provided by The Royal Horticultural Society of Great Britain. Common color names are also occasionally used.

Tree:

*Size*.—Generally considered medium to medium-large in its growth pattern as compared to other common commercial nectarine cultivars ripening in the late season of maturity. The tree of the present variety was pruned to a height of approximately 270.0 cm. to about 310.0 cm. at commercial maturity. Fruit size can vary with crop load and the conditions under which the fruit and tree are grown.

*Width*.—Approximately 265.0 cm.

*Vigor*.—Considered moderately vigorous. The present peach tree variety grew from about 175.0 cm. to about 180.0 cm. in height during the first growing season. The new variety was pruned to a height of approximately 150.0 cm. during the first dormant season, and primary scaffolds were then selected for the desired tree structure.

*Productivity*.—Productive. Fruit set varies from more than the desired crop load, to levels higher than desired amounts, when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the cultural practices employed.

*Fruit bearing*.—Regular. Fruit set has been more than adequate during the previous years of observation, and thinning was necessary during the past 10 years on both the original seedling and on subsequent asexually reproduced trees.

*Tree form*.—Upright, and pruned into a vase shape.

*Density*.—Considered moderately dense. It has been discovered that pruning the branches from the center of the tree to obtain a resulting vase shape allows for enhanced air movement and appropriate amounts of sunlight to improve fruit color, and renewal of fruiting wood throughout the tree.

*Hardiness*.—The present tree was grown and evaluated in USDA Hardiness Zone 9. The calculated winter chilling requirements of the new tree is approximately 600 hours at a temperature below 7.0 degrees C. The present variety appears to be hardy under typical central San Joaquin Valley climatic conditions.

Trunk:

*Diameter*.—Approximately 22.0 cm in diameter when measured at a distance of approximately 15.5 cm. above the soil level. This measurement was taken at the beginning of the 11th growing season.

*Bark texture*.—Considered moderately rough, with folds of papery scarfskin being present. Since bark development and coloration change with advancing tree age this characteristic varies with the tree vigor, age and regional conditions.

*Lenticels*.—Numerous flat, oval lenticels are present. The lenticels range in size from approximately 5.0 millimeters to about 7.0 mm. in width, and between about 1.0 and about 2.5 millimeters in height. The development and size of the trunk lenticels can be influenced, to some degree, by the ambient growing conditions. As trees of this variety mature, lenticels are present, but they are generally covered by increasing layers of cork (mature bark) and therefore become less apparent.

*Lenticel color*.—Considered an orange brown, (RHS Greyed-Orange Group 165 B).

*Bark coloration*.—Variable, but it is generally considered to be a greyed brown, (RHS Grey-Green Group 197 B). This bark description was taken from trees in their tenth leaf which have ruptured the scarf skin, and which also have developed bark furrowing which is much more typical of the bark of older trees. It should be noted that the coloration of the bark is influenced, and varies, as the smoother, darker background color approaches other bark features such as the lenticels, and the initial fissures which form a feature of the scarf skin development.

Branches:

*Size*.—Considered medium large for the variety.

*Diameter*.—Average as compared to other peach varieties. The branches have a diameter of about 11.0 centimeters when measured during the 10th year after grafting.

*Flowering shoot thickness*.—Average for the species. Generally, the most consistent flower bud development and therefore potential fruiting sites occur on shoots which are approximately 5.0 millimeters in diameter or larger but generally less than 13.0 millimeters in diameter at the time of bloom.

*Flowering shoot anthocyanin coloration*.—Absent.

*Surface texture*.—Average, and appearing relatively smooth but with more furrowing on wood which is several years old.

*Crotch angles*.—Primary branches are considered variable, and are usually growing at an angle of about 42 to about 46 degrees when measured from a horizontal plane.

*Current season shoots*.—Surface texture — Substantially glabrous.

*Internode length*.—Approximately 2.6 cm.

*Color of mature branches*.—Approximately Grey brown, (RHS Greyed-Orange Group 177 A).

*Current season's shoots*.—Color. — Light green, (RHS Yellow-Green Group 145 B). The color of new shoot tips is considered a bright and shiny green (RHS Yellow-Green Group 146 D). The vegetative shoot color can be significantly influenced by plant nutrition, irrigation practices, and exposure to sunlight, and therefore should not be considered a consistent botanical characteristic of this new variety.

Leaves:

*Size*.—Considered somewhat elongated and narrow for the species. Leaf measurements have been taken from vigorous, upright, current-season growth, at approximately mid-shoot. The leaf size is often influenced by prevailing growing conditions, quality and intensity of available sunlight, and the location of the leaf within the tree canopy. For this reason, leaf sizes can vary significantly based upon the ambient and other cultural factors listed above.

*Leaf bud burst*.—Medium.

*Leaf length*.—Approximately 145.0 to about 160.0 millimeters.

*Leaf width*.—Approximately 32.0 to about 36.0 millimeters.

*Leaf base-shape*.—The leaves generally exhibit equal marginal symmetry relative to the leaf longitudinal axis.

*Leaf form*.—Lanceolate.

*Leaf tip form*.—Acuminate.

*Leaf color*.—Upper Leaf Surface — Medium green, (approximately RHS Green Group 137 B).

*Leaf texture*.—

*Upper leaf surface*.—Glabrous.

*Lower leaf surface*.—Glabrous.

*Leaf color*.—Lower Leaf Surface — Medium green, (approximately RHS Yellow-Green Group 146 A).

*Leaf venation*.—Pinnately veined.

*Mid-vein*.—Color — Considered a pale green, (approximately RHS Yellow-Green Group 145 C) in the early to mid-period of the growing season.

*Leaf margins*.—Gently undulating.

*Form*.—Considered crenulate.

*Uniformity*.—Generally uniform.

*Leaf petioles*.—

*Form*.—Considered canaliculated, and having a more pronounced trough when viewed from the dorsal aspect. The petiole margin is considered rounded when viewed from the ventral aspect.

*Size*.—Considered medium-small for the species.

*Length*.—About 9.0 to about 12.0 mm.

*Diameter*.—About 1.5 to about 2.0 mm.

*Color*.—A yellowed green, (approximately RHS Yellow-Green Group 146 C).

*Texture*.—Glabrous.

*Strength*.—Durable for species until senescence.

*Leaf glands*.—

*Size*.—Considered relatively small for the species; approximately 1.5 mm. in length; and about 1.0 mm. in height.

*Number*.—Generally one and less common two glands appear per marginal side are found. Observations of more than two glands per marginal side are very uncommon.

*Type*.—Glands located at the base of the leaf are predominantly reniform in shape. An additional one to two, or occasionally more glands, which appear reniform, and stalked, are often present at the basal margin of the leaf petiole as well.

*Color*.—Considered a yellowed green, approximately (RHS Yellow-Green Group 151 A). Typically, the coloration of the glands darkens, and occasionally begins to desiccate during the mid-late growing season.

*Leaf stipules*.—

*Size*.—Medium large for this variety.

*Number*.—Typically 2 per leaf bud, and up to 6 per shoot tip.

*Form*.—Lanceolate in form, and having a serrated marginal edge.

*Color*.—Green, (approximately RHS Yellow-Green Group 145 A) when young, but graduating to a brown color, (approximately RHS Greyed-Orange Group 165 A) with advancing senescence. The leaf stipules are generally considered to be early deciduous.

Flower buds:

*Hardiness*.—No winter injury (bud death) has been noted during the last several years of observation in the central San Joaquin Valley. The new variety of nectarine tree has not been intentionally subjected to drought, cold or heat stress, and therefore this information is not available.

*Flower bud*.—Size — Variable, and dependent on the state of maturity. The flower buds as described were observed approximately 7 days prior to bloom.

*Length*.—Approximately, 15.5 millimeters.

*Diameter*.—Approximately, 8.5 millimeters.

*Surface texture*.—Pubescent.

*Orientation*.—Considered appressed, but appear less so as the blossoms near opening.

*Bud scale color*.—Approximately RHS Greyed-Orange Group 175 A.

Flowers:

*Date of first bloom*.—Observed on Feb. 24, 2017.

*Blooming time*.—Considered average in relative comparison to other commercial peach cultivars grown in the central San Joaquin Valley. The date of full bloom was observed on Mar. 2, 2017. The date of full bloom varies slightly with climatic conditions, and prevailing cultural practices.

*Duration of bloom*.—Approximately 8 or more days. This characteristic varies slightly with the prevailing climatic conditions.

*Flower class*.—Considered a perfect flower, complete and perigynous.

*Flower type*.—The variety is considered to have a showy type flower.

*Flower size*.—Considered large. The flower diameter at full bloom, is approximately 35.0 to 42.0 millimeters.

*Bloom quantity*.—Considered abundant.

*Flower bud density*.—Generally considered dense.

*Flower bud frequency*.—Generally, two flower buds appear per node, occasionally one flower bud per node is observed. Very rarely three floral Bud's per node are observed.

*Petal size*.—Generally considered large for the species.

*Petal length*.—Approximately 18.0-20.0 millimeters.

*Petal width*.—Approximately 11.0 to 14.0 millimeters.

*Petal form*.—Considered broadly ovate.

*Petal count*.—Nearly always 5.

*Petal texture*.—

*Upper petal texture*.—Very finely pubescent, satin like.

*Lower petal texture*.—Very finely pubescent, satin like.

*Petal color*.—Considered a light pink at the popcorn stage, (RHS Red-Purple Group 62 D), and darkening with advanced senescence, and the exposure of sunlight, to a medium-dark pink, (RHS Red-Purple 63 C). This darkening of the petal is generally most present within the margins of the petal claw.

*Fragrance*.—Slight.

*Petal claw*.—

*Form*.—The claw is considered ovate, and is generally large.

*Length*.—Approximately 12.0 millimeters.

*Width*.—Approximately 10.0 millimeters.

*Petal margins*.—Generally, slightly undulate.

*Petal apex*.—Entire.

*Flower pedicel*.—

*Length*.—Considered medium with an approximate length of about 1.0 to about 2.0 millimeters.

*Diameter*.—Approximately 1.0-1.5 millimeters.

*Color*.—A medium brown, approximately (RHS Grey-Brown Group N199 D) depending on pedicel and fruit maturity and timing of visual observance.

*Strength*.—Tenacious. Average for the species.

*Texture*.—Generally smooth to slightly undulate.

*Floral nectaries*.—

*Color*.—Considered a vibrant orange, (approximately RHS Greyed-Orange Group 170 B).

*Calyx*.—

*Surface texture*.—Generally glabrous.

*Color*.—Approximately RHS Greyed-Purple Group 183 B.

*Sepals*.—

*Upper surface texture*.—Moderately pubescent.

*Lower surface texture*.—Glabrous.

*Number*.—5 sepals.

*Size*.—Considered medium.

*Sepal length*.—Approximately 4.0 to 6.0 millimeters.

*Sepal width*.—Approximately 4.5 to 6.0 millimeters.

*Sepal shape*.—Generally obovate.

*Sepal margin*.—Considered smooth and entire.

*Sepal color*.—Approximately RHS Greyed-Purple Group 183 A.

*Anthers*.—

*Generally*.—Average in size.

*Color*.—Yellow when viewed dorsally and prior to dehiscence, (approximately RHS Yellow-Orange Group 20 A).

*Position relative to stigma*.—Generally, the stigma is superior to the anthers by approx. 1.0-2.0 millimeters.

*Pollen production*.—Pollen is abundant and has a yellow color, (approximately RHS Yellow-Orange Group 20 A).

*Fertility*.—Self-fertile.

*Filaments*.—

*Size*.—Approximately 14.0 to 17.0 millimeters in length.

*Color*.—Considered white to a pinkish-white, (RHS White Group N155 D).

*Stamen*.—

*Number*.—Generally, 25 to 30 per flower.

*Pistil*.—

*Number*.—Usually one, and only rarely more than one.

*Generally*.—Considered medium in size.

*Length*.—Approximately 17.0 to about 19.0 millimeters in length including the ovary.

*Ovary*.—Glabrous.

*Color*.—Considered a very pale green, (approximately RHS Yellow-Green Group 150 D).

*Surface texture*.—The variety has a long glabrous pistil.

*Position relative to petals*.—At flower maturity the stamens grow to be superior to the petals.

Fruit:

*Maturity when described*.—Firm ripe condition (shipping ripe).

*Date of first picking*.—Approximately Sep. 10, 2017.

*Date of last picking*.—Sep. 21, 2017. The date of harvest can vary with the prevailing climatic conditions, crop loads and the current climatic and cultural practices.

*Size*.—Generally — Considered medium large.

*Average cheek diameter*.—Approximately 76.0 to about 80.0 millimeters.

*Average axial diameter*.—Approximately 74.0 to about 79.0 millimeters.

*Typical weight*.—Approximately 225.0 grams. The fruit size and weight can vary and are dependent on the prevailing cultural practices and growing conditions.

*Fruit form*.—Generally — Considered globose. The fruit is generally very uniform in symmetry.

*Mucron tip*.—Absent.

*Fruit suture*.—No stitching exists along the suture line.

*Suture*.—Color — Generally, the fruit appears blushed to the same degree as the skin, (approximately RHS Orange-Red Group 34 A).

*Ventral surface*.—Form — Considered even, and uniform in appearance, when it is viewed from the lateral, sutural plane.

*Apex*.—Shape — Rounded to slightly rutuse.

*Base*.—Shape — Generally smooth.

*Stem cavity*.—Generally — It extends in a rounded circular form which is generally considered uniform. The stem cavity is rounded but slightly extended toward the suture. The average depth of the stem cavity is about 8.0-10.0 mm. The average width of the stem cavity is about 26.0 mm. The average length of the stem cavity, when measured in the suturial plane is about 45.0 mm.

*Fruit skin*.—

*Thickness*.—Considered medium in thickness, and tenacious to the flesh.

*Surface texture*.—Glabrous.

*Taste*.—Non-astringent.

*Tendency to crack*.—Not observed in the previous years of observation and evaluation.

*Fruit skin color*.—

*Blush color*.—Generally speaking, a red blush exists on a majority of the skin of the fruit (approximately RHS Orange-Red Group 34 A), and is more typically present on the portions of the fruit facing the sunlight. The blush of the fruit typically covers approximately 75%-95% of the fruit skin surface. The percentage of the blush on the fruit skin surface can vary, and is generally dependent upon the fruit's exposure to direct sunlight; specific fruit maturity; and also the prevailing ecological and cultural conditions under which the fruit was grown.

*Ground color*.—A medium light orange yellow, (approximately RHS. Yellow-Orange Group 23 C). The ground color of the fruit can vary significantly based upon the maturity of the fruit when this measurement is taken and generally gains a lighter and less green cast with higher maturity.

*Fruit anthocyanin coloration*.—Anthocyanin is strong around the stone and radiates into the flesh in a descending gradient. No anthocyanin is observed near the skin.

*Fruit glossiness*.—Fruit is considered to be glossy.

*Fruit stem*.—

*Size*.—Medium in length, approximately 6.0 to about 8.0 millimeters.

*Diameter*.—Approximately 2.0 to about 3.0 millimeters.

*Color*.—Pale yellow-green, (approximately RHS Yellow-Green Group N144 C).

*Fruit flesh*.—

*Ripening*.—Considered even.

*Texture*.—Firm, crunchy, juicy and dense. Considered firm-melting in flesh classification.

*Lenticels*.—Medium.

*Fibers*.—Present but not prominent.

*Aroma*.—Slight.

*Eating quality*.—Considered very good.

*Flavor*.—Considered balanced with sweetness and acidity.

*Juice production*.—Moderate.

*Brix*.—About 11.0 to 13.5 degrees. This characteristic varies slightly with the number of fruit per tree; the maturity of fruit when harvested; the prevailing cultural practices; and the ambient climatic conditions.

*Acidity*.—Considered medium. Approximately 0.7 titratable acidity. Acid levels assayed from fruit flesh can vary with fruit maturity, sunlight exposure, and climatic, regional, seasonal and cultural influences.

*Flesh color*.—It is considered yellow, (approximately RHS Yellow-Orange Group 17 D), slight pigmentation of pink red can be seen radiating from the stone (approximately RHS Red Group 39 A).

Stone:

*Type*.—Considered a clingstone.

*Size*.—It is generally considered to be medium for the species. The stone size varies significantly depending upon the tree vigor, the crop load, and the prevailing growing and cultural conditions under which the tree was grown.

*Length*.—Average, about 30.0 to about 35.0 millimeters.

*Width*.—Average, about 23.0 to about 27.0 millimeters.

*Diameter*.—Average, about 17.0 to about 20.0 millimeters.

*Form*.—Roughly ovoid.

*Stone base*.—Shape — The stone is considered shortly attenuate.

*Apex*.—Shape — The stone exhibits a slight acute apex.

*Stone surface*.—

*Surface texture*.—Considered irregularly furrowed toward the apex. Further, more pitting exists in the mid-portion of the stone (laterally), and is more common toward the base.

*Ridges*.—Ridging is generally more prominent, and is usually oriented parallel, and laterally relative at the ventral and dorsal margins.

*Ventral edge*.—The ventral edge is generally is described as having adjoining ridges formed from each hemisphere. There are longitudinal grooves running alongside this joined ventral suture. Secondarily there can exist an additional set of parallel ridges, one on each side of the major ridge. These secondary ridges are less prominent and do not always extend from the hilum to the apex.

*Dorsal edge*.—Shape — Generally considered even. The folds of the surface ridges appearing on the external margins often end gently along the suture.

*Stone color*.—The color of a mature, dry stone is generally considered a dull brown, approximately (RHS Greyed-Orange Group 165 D). Stone color can vary considering how recently the fruit has ripened, degree of oxidation, and blanching due to exposure sunlight.

*Tendency to split*.—Splitting has rarely been noted.

*Kernel.*—

*Length.*—Approximately 16.0-19.0 millimeters.

*Width.*—Approximately 12.0-15.0 millimeters.

*Thickness.*—4.0-6.0 millimeters.

*Size.*—The kernel is considered medium in size.

*Form.*—Considered generally ovoid.

*Kernel surface texture.*—Kernel pellicle is shortly pubescent.

*Color.*—A dark tan (RHS Greyed-Orange Group 165 C).

*Use.*—The present variety 'Burnectthirtyfour' is considered to be a nectarine tree of the late season of maturity, and which produces fruit which are considered to be firm, attractively colored, and which are useful for both local and long distance shipping.

*Keeping quality.*—Appears excellent. The fruit of the present variety has stored well for periods of up to 35 days after harvest at 1.0 degree Celsius.

*Shipping quality.*—Good. The fruit of the new nectarine tree variety showed minimal bruising of the flesh or skin damage after being subjected to normal harvesting and packing procedures.

*Resistance to insects and disease.*—No particular susceptibilities were noted. The present variety has not been intentionally tested to expose or detect any susceptibilities or resistances to any known plant, fruit diseases, insect, frost, winter injury or other environmental factors.

Although the new variety of nectarine tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of nectarine tree, what we claim is new, and desire to secure by plant Letters Patent is:

1. A new distinct variety of nectarine tree, substantially as illustrated and described, and which is characterized principally as to novelty by producing an attractively colored yellow-fleshed, clingstone nectarine which is mature for harvesting and shipment approximately September 10 to September 21 under the ecological conditions prevailing in the San Joaquin Valley of central California.

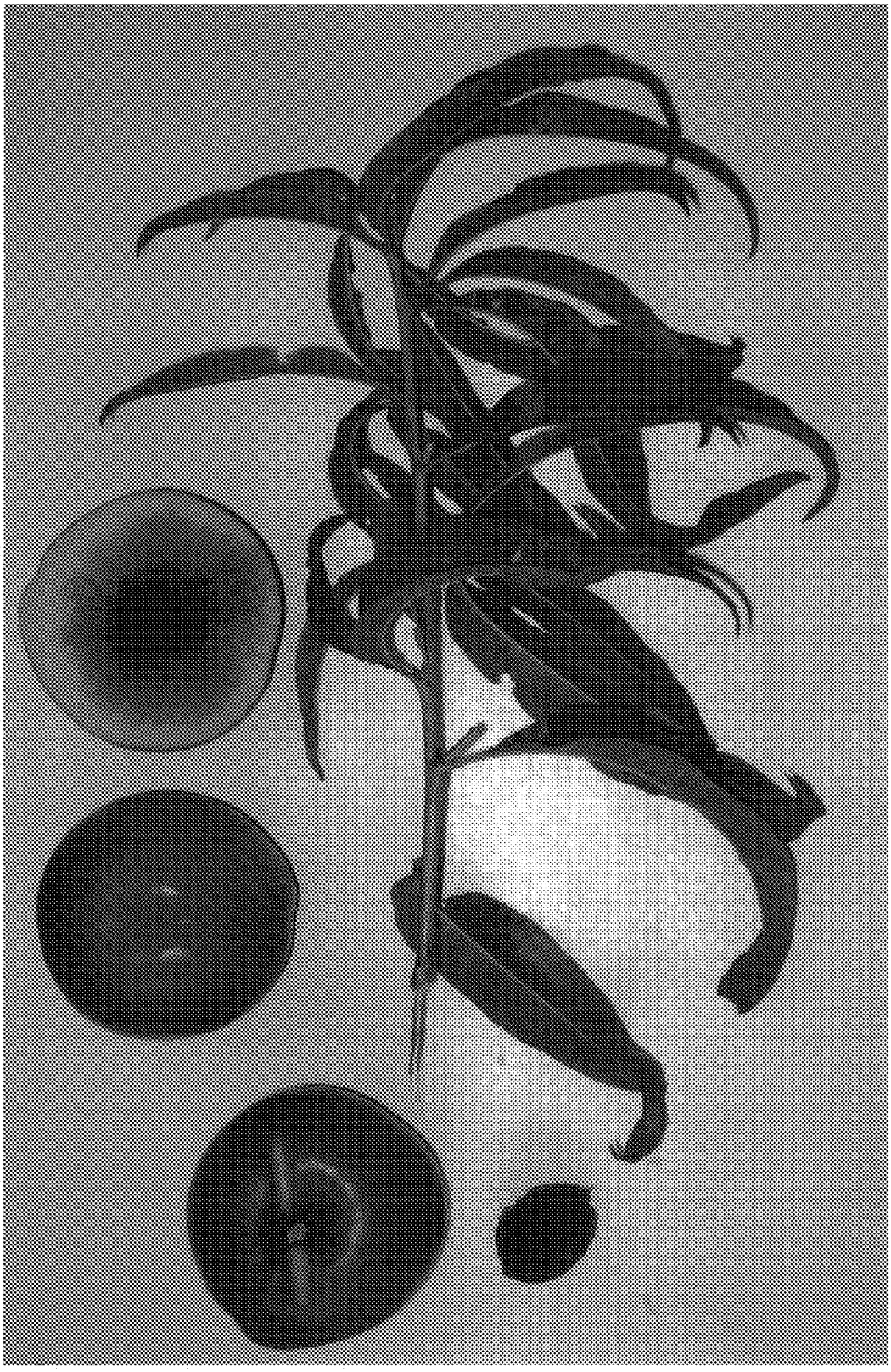

* * * * *